(12) United States Patent
Grabiner et al.

(10) Patent No.: US 8,990,041 B2
(45) Date of Patent: Mar. 24, 2015

(54) FALL DETECTION

(75) Inventors: Mark D. Grabiner, Chicago, IL (US);
Kenton R. Kaufman, Rochester, MN (US); Barry K. Gilbert, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 672 days.

(21) Appl. No.: 13/266,437

(22) PCT Filed: Apr. 27, 2010

(86) PCT No.: PCT/US2010/032546
§ 371 (c)(1),
(2), (4) Date: Jan. 11, 2012

(87) PCT Pub. No.: WO2010/126878
PCT Pub. Date: Nov. 4, 2010

(65) Prior Publication Data
US 2012/0101770 A1  Apr. 26, 2012

Related U.S. Application Data

(60) Provisional application No. 61/173,040, filed on Apr. 27, 2009.

(51) Int. Cl.
*G06F 19/00* (2011.01)
*G01P 3/00* (2006.01)
(Continued)

(52) U.S. Cl.
CPC ............ *A61B 5/1117* (2013.01); *A61B 5/1116* (2013.01); *A61B 5/7275* (2013.01); *A61B 2562/0219* (2013.01)

USPC ........................................ 702/141; 280/730.1

(58) Field of Classification Search
CPC ............................ A61B 5/1117; A61B 5/7264
USPC ........... 702/141, 86, 92, 158, 166; 280/730.1; 340/539.12, 573.1; 473/353; 482/54
See application file for complete search history.

(56) References Cited

U.S. PATENT DOCUMENTS 6,113,504 A   9/2000  Kuesters
6,160,478 A   12/2000 Jacobsen et al.
(Continued)

FOREIGN PATENT DOCUMENTS

EP     0849715 A2    6/1998
WO     2006009970 A2 1/2006
(Continued)

OTHER PUBLICATIONS

Gupta, S. Das. Optimum Classification Rules for Classification into Two Multivariate Normal Populations. The Annals of Mathematical Statistics 36 (1965), No. 4, 1174-1184. doi:10.1214/aoms/1177699990. http://projecteuclid.org/euclid.aoms/1177699990.*
(Continued)

*Primary Examiner* — John H Le
(74) *Attorney, Agent, or Firm* — Shumaker & Sieffert, P.A.

(57) ABSTRACT

A fall detection device may be uniquely associated with a wearer. The fall detection device may predict whether a fall event is imminent based on kinematic information of the wearer's body. The device may also confirm whether the wearer actually experienced a fall event based on additional kinematic information.

21 Claims, 6 Drawing Sheets

(51) Int. Cl.
  G01B 21/06 (2006.01)
  G01P 15/00 (2006.01)
  A61B 5/11 (2006.01)
  A61B 5/00 (2006.01)

(56) References Cited

U.S. PATENT DOCUMENTS

| | | | |
|---|---|---|---|
| 6,433,690 | B2 | 8/2002 | Petelenz et al. |
| 6,998,978 | B2 | 2/2006 | Kirkeby |
| 2005/0067816 | A1* | 3/2005 | Buckman .................. 280/730.1 |
| 2005/0110648 | A1 | 5/2005 | Lehrman et al. |
| 2006/0247104 | A1 | 11/2006 | Grabiner et al. |

FOREIGN PATENT DOCUMENTS

| | | |
|---|---|---|
| WO | 2007057692 A2 | 5/2007 |
| WO | 2010037564 A1 | 4/2010 |

OTHER PUBLICATIONS

Communication from counterpart European application No. 10716234.9, dated Feb. 12, 2014, 5 pp.

Kara E. Bliley et al., Design of Posture and Activity Detector (PAD), Proceedings of the 29th Annual International Conferece of the IDDD EMBS Cite Internationale, Lyon, France Aug. 23-26, 2007, 5 pages.

Kadoya et al., "Evaluation by Accelerometry of Walking Patten Before Falls in Hemiplegic Patients", 2001 Proceedings of the 23rd Annual EMBS International Conference, Oct. 25-28, Istanbul, Turkey, 2 pages.

Marschollek et al., "Assessing elderly persons' fall risk using spectral analysis on accelerometric data—a clinical evaluation study", 30th Annual International IEEE EMBS Conference, Vancouver, British Columbia, Canada, Aug. 20-24, 2008, 4 pages.

Kara E. Bliley et al. "Design of a Compact Sysem Using a MEMS Accelerometer to Measure Body Posture and Ambulation", Procceedings of the 19th IEEE Symposium on Computer-Based Medical Systems, 2006, 4 pages.

Kara E. Bliley et al., "A Miniaturized Low Power Personal Motion Analysis Logger Utilizing MEMS Accelerometers and Low Power Microcontroller", Proceedings of the 3rd Annual International IEEE EMBS Special Topic Conference on Microtechnologies in Medicine and Biology, Kahuku, Oahu, Hawaii, May 12-15, 2005, 2 pages.

Rauser et al., "Lifelong heterogeneity in fecundity is insufficient to explain late-like fecundity plateaus in *Drosophila melanogaster*", Experimental Gerontology, vol. 40, pp. 660-670, Aug. 8, 2005.

Notification Concerning Transmittal of International Preliminary Report on Patentability (Chapter I of the Patent Cooperation Treaty) for corresponding application No. PCT/US2010/032546, mailed Nov. 10, 2011, 9 pages.

Notification of Transmittal of the International Search Report and Written Opinion of the International Searching Authority, or Declaration for corresponding application No. PCT/US2010/032546, mailed Jul. 22, 2010, 14 pages.

Quagliarella et al., "An Interactive Fall and Loss of Consciousness Detector System", Gait & Posture, vol. 28, pp. 603-702, 2008.

Kangas et al., "Comparison of Low-Complexity Fall Detection Algorithms for Body Attached Accelerometers", Gait & Posture, vol. 28, pp. 285-291, 2008.

Nyan et al., "Application of Motion Analysis in Pre-Impact Fall Detection", Journal of Biomechanics, vol. 41, pp. 2297-2304, 2008.

MiniSun, "IDEEA Overview, A Device for Analyzing Body Motion", http://www.minisun.com/ideea_overview.asp, 2 pages, Aug. 16, 2006.

Carnegie Mellon University, "eWatch—overview", http://flat-earth.ece.cmu.edu/~eWatch/, 2 pages, Aug. 16, 2006.

A-Pōd, "Success You Can Measure. Introduction to the A-Pōd™ Sport Performance System", 6th Dimension Devices, Inc., www.6dd.ca, 1 page, 2006.

* cited by examiner

FALL DETECTION

CROSS REFERENCE TO RELATED APPLICATIONS

This application claims the benefit of U.S. Provisional Application No. 61/173,040, filed Apr. 27, 2009, which is incorporated herein by reference in its entirety.

STATEMENT REGARDING FEDERALLY SPONSORED RESEARCH AND DEVELOPMENT

This invention was made with United States government support awarded by the National Institute of Health, Grant Numbers AG010557 and AG016778, and the Centers for Disease Control, Grant Number R49 CE000620. The United States government has certain rights in this invention.

TECHNICAL FIELD

The disclosure relates to posture and activity detection, and more specifically to fall detection.

BACKGROUND

Falls and fall related injuries are among the most common, costly and serious medical problems facing the elderly. Every year, one-third to one-half of the population age 65 and over experience falls. Falls are the leading cause of trauma related deaths and injuries in adults 65 years and older. Half of the elderly people who fall do so repeatedly. In 2000, the direct cost of all fall injuries to older adults was slightly more than $19 billion. In addition, falling experience can lead to a loss of balance confidence and fear of falling. Fear of falling can in turn lead to a loss of mobility and balance deterioration, which further increases the likelihood of a fall. Loss of independence can result from both fracture-related disability and self-imposed limitations caused by fear of falling. Decreased confidence in the ability to ambulate leads to reduced mobility and further functional decline, depression, feelings of helplessness, and social isolation.

For the past 20 years a system has been available in which the individual wears an electronic pendant on a chain around the neck and is instructed to push a button on the pendant following a fall. If they push the button successfully, help is dispatched from a central call center to the individual's residence. However, if the individual is incapacitated when they fall and are unable to push the button, the fact that they fell and are incapacitated may go unrecognized for many hours or days.

A similar system has been recommended for use in eldercare facilities. In such facilities, personnel are typically on duty 24/7. If the "button push" is successful, help can be dispatched immediately to assist the downed resident from within the building. Again, however, if individuals are incapacitated and unable to push the button, significant amounts of time may elapse before they are discovered.

SUMMARY

In general, the disclosure relates to a fall detection device that may be uniquely associated with a wearer. The fall detection device may predict and confirm a fall experienced by the wearer based on kinematic information of the wearer.

In one example, the disclosure is directed to a device, comprising at least one kinematic sensor that measures kinematic information associated with a wearer of the device, the kinematic information including threshold kinematic information and fall event kinematic information, and a controller that analyzes the threshold kinematic information to determine whether a threshold indicative of a postural disturbance is satisfied, and determines whether a fall event is imminent based on the fall event kinematic information. The at least one kinematic sensor may include one or more of an accelerometer, a magnetometer, a pressure sensor, an altimeter, a velocity sensor, an angular velocity sensor or a gyroscope. The kinematic information may include at least one of a displacement, a velocity, an acceleration, or a jerk.

In another example, the disclosure is directed to a method comprising receiving threshold kinematic information associated with movement of a user, determining whether the threshold kinematic information satisfies a threshold indicative of a postural disturbance that may lead to the user experiencing a fall event, receiving fall event kinematic information associated with movement of the user subsequent to satisfaction of the threshold, and predicting whether the user will experience a fall based on the fall event kinematic information.

In another example, the disclosure is directed to a device, comprising at least one kinematic sensor that measures threshold kinematic information associated with movement of a wearer of the device, the threshold kinematic information including at least one of a linear acceleration or a rotational acceleration, a linear or a rotational velocity, or displacement, a controller that identifies a time of postural disturbance at which the threshold kinematic information satisfies a threshold indicative of a postural disturbance that may lead to the user experiencing a fall event, and at least one kinematic sensor that measures fall event kinematic information associated with movement of the wearer subsequent to satisfaction of the threshold, fall event kinematic information including at least one of a linear or angular acceleration at a first predetermined time after the time of postural disturbance, wherein the controller further predicts whether the user will experience a fall based on the fall event kinematic information.

The details of one or more examples are set forth in the accompanying drawings and the description below. Other features and advantages will be apparent from the description, drawings, and from the claims.

DETAILED DESCRIPTION

Figure 1:
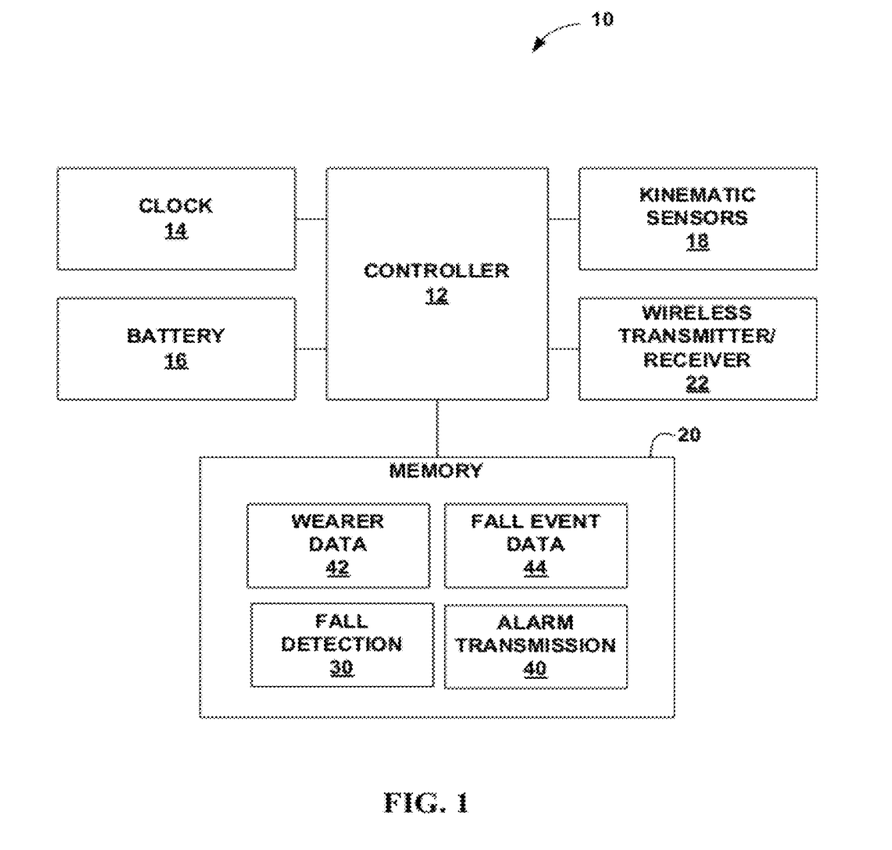
FIG. 1 is a block diagram illustrating an example fall detection device.

FIG. 1 is a block diagram illustrating an example fall detection device 10. Fall detection device 10 is associated with a wearer, such as an elderly person in their home or as a resident of an eldercare living facility. Fall detection device 10 may also be associated with other persons who would benefit from fall monitoring, such as memory care patients, orthopedic patients, critical care patients, sleep disorder patients, cardiac patients, stroke patients, paraplegic or quadriplegic persons, persons with head injuries, persons with vertigo, persons with MS, CS or other neurological diseases, etc.

Falls may generally be classified with reference to the direction of the fall, e.g., forward falls ("trips"), backward falls ("slips"), or right side or left side ("right lateral" or "left lateral") falls. Fall detection device 10 detects falls using a fall detection algorithm. The person to be monitored wears a fall detection device 10. For convenience, this device may be, for example, approximately the size of a US quarter. One example hardware implementation that may be used for fall detection device 10 is described in *"Design of Posture and Activity Detector (PAD),"* 2007 *Annual International Conference of the IEEE Engineering in Medicine and Biology Society Conference Proceedings:* 2659-63. However, it shall be understood that this is an example only, and that the disclosure is not limited in this respect.

In general, fall detection device 10 may include the following elements: a battery 16, a processor or controller 12, one or more kinematic sensors 18, data/program storage such as memory 20, an electronic time-of-day "clock" 14, and a wireless transmitter chip 22. Kinematic sensors 18 may include, for example, one or more of an accelerometer, a magnetometer, a pressure sensor, an altimeter, a displacement sensor, a velocity sensor, an angular velocity sensor, a gyroscope, or other sensor capable of measuring kinematic information. The kinematic information measured by kinematic sensors 18 may include, for example, one or more of a displacement, a velocity, an acceleration, or a jerk. The kinematic information may be measured in any direction, including, for example, in one or more of the three orthogonal directions, the x (anteroposterior or "AP"), y (medial-lateral or "ML") and z (vertical) directions. The kinematic information may include one or more linear kinematic terms and/or one or more rotational (angular) kinematic terms.

Each type of kinematic information may be measured by a designated sensor or may be derived from information obtained from one or more kinematic sensors. For example, vertical displacement may be measured by a designated sensor or may be calculated based on acceleration or velocity data One or more data storage devices, represented generally by memory 20, store information, such as data and/or software modules, associated with device 10. Memory 20 may be implemented in any of several different ways. For example, memory 20 may include one or more different types of memory, e.g., random access memory (RAM), electrically erasable programmable read-only memory (EEPROM), FLASH memory, etc. Some portions of memory 20 may be collocated on-chip with controller 12 (e.g., in the case of microcontroller) or may be on a separate component (e.g., in the case of a FLASH memory or EEPROM).

Regardless of the implementation, memory 20 includes a fall detection module 30. Memory 20 may also include an alarm transmission module 40. Fall detection module 30 and alarm transmission module 40 are software modules executed by the controller and stored in memory 20. Fall detection module 30 includes software that, when executed by controller 12, detects and may in some cases predict (for example, by a few hundred milliseconds) an imminent fall, that is, a fall that will be experienced by the wearer (for example, within an additional few hundred milliseconds) based on the kinematic information obtained from kinematic sensors 18. Fall event data 44 is also stored in memory 20. Fall event data 44 may include, for example, the kinematic information obtained by kinematic sensors 18, data generated by fall detection module 30 during analysis of the kinematic information, or data generated by alarm transmission module 40 during generation of an alarm signal, or any other data or software modules received or generated by device 10.

Detection of such a fall is referred to herein as a "fall event." Fall detection algorithm 30 may also discriminate between those postural disturbances that lead to a fall and those that do not lead to a fall, such as a stumble. Memory 20 may also store wearer data 42. Wearer data 42 may include, for example, identification information such as the wearer's name, address, telephone number(s), social security number, patient id, etc.; vital statistics such as birth date, age, height, weight, etc.; health information such as blood type, medical conditions, medical alerts, prescription information, etc.; and/or any other data that may either identify the wearer and/or provide pertinent medical information to an assistance provider upon detection of a fall event.

Alarm transmission module 40 includes software that, when executed by the controller, generates and/or transmits one or more fall event signals indicating that a fall event has been detected. The fall event signal may include a time/date information associated with the fall event, at least some of the wearer data sufficient to identify the person associated with the fall event and/or any pertinent medical information that may prove important to an assistance provider receiving the fall event alarm. The fall event signal may be sent to a remote or local monitoring station, which may be a standalone or networked computer or other electronic device such as a cell phone, laptop, PDA, pager, etc. The fall event signal may be received directly by the monitoring station or may be received and forwarded via one or more intermediate wireless transceivers, satellite, cellular network, or the internet. The fall event signal may take any form of wired or wireless communication, e-mail, text message, page, voice mail, or other form of electronic communication.

Fall detection device 10 detects fall events based on the kinematic information obtained by one or more kinematic sensors 18 as a result of a postural disturbance. As mentioned above, for example, the kinematic information may be quantified based on one or more kinematic measurements of the wearer's body, such as the displacement, velocity, acceleration, jerk (rate of change of acceleration), and/or others. These kinematic measurements may be linear or rotational. The kinematic measurements may be taken at one or more appropriate points on the wearer's body. For example, one location at which kinematic information may be relevant to the determination of a fall event is the center of mass (COM) of the trunk. To obtain kinematic information concerning the COM, fall detection device 10 may be worn in contact with or immediately next to the trunk of the body. However, any position on the body which allows the device to obtain meaningful kinematic information may be used. In some examples, fall detection device 10 may be worn at chest level and be held in place by an adjustable or elastic chest strap, within a custom or off-the-shelf brassier-style garment, as a pendant on a neck chain, with the neck chain also serving as the transmitting and receiving antenna for the wireless communication link, within some other close fitting garment, or using any other means by which a device may be held in close proximity to the trunk of the body.

To detect fall events and/or to discriminate between fall events and recovery events, fall detection module 30 is programmed based on analysis of data obtained from experiments in which postural disturbances, the magnitude and direction of which were experimentally controlled, were delivered to subjects in a sample population. In these example experiments, standardized forward-directed and backward-directed postural disturbances were delivered by a microprocessor controlled motorized platform. The platform simulated common balance challenges such as a bump from behind, a slip on a slick surface, or a stumble over an obstacle. An example of such a motorized platform is available as the ActiveStep® mobility simulator, from Simbex LLC, Lebanon, N.H. The disturbances included those that were sufficient to cause a fall and those that did not result in a fall. The disturbances were implemented in laboratory designed environments to reflect real world activities by inducing a fall during locomotion instead of simulating staged falls from static positions.

For example, a standardized forward-directed disturbance accelerated the treadmill belt backwards from 0 to 6.5 m/s$^2$ in 0.5 seconds. A standardized backward-directed disturbance accelerated the treadmill belt forward from 0 to 10 m/s$^2$ in 0.14 seconds. The initial disturbance exposure caused all subjects to lose their balance and fall into a safety harness. Subsequently, a brief training protocol, during which the subject was exposed to increasingly and then decreasingly challenging postural disturbances, was subsequently administered. After the training protocol, the standardized disturbance was again delivered and all subjects successfully recovered.

Capture of kinematic information from one or more kinematic sensors was used to quantify the biomechanics of the subjects' response to the postural disturbance. Anteroposterior (x), mediolateral (y), and vertical (z) linear displacements and accelerations of the trunk center of mass (COM) were calculated during the standardized disturbances. For example, trunk displacement and acceleration at 50-350 ms following the disturbance were computed at 50 ms intervals. The statistical significance between-group (fall vs. non-fall) differences were investigated using paired t-tests. The variables with significant between group differences were used in a stepwise discriminant analysis, the intent of which was to distinguish group membership as either a "fall event" or a "recovery event" (e.g., non-fall) based on subject-specific values of the variables. Based on the example experimental process, certain of the kinematic information may be identified as being predictive of a fall or a recovery.

Figure 2:
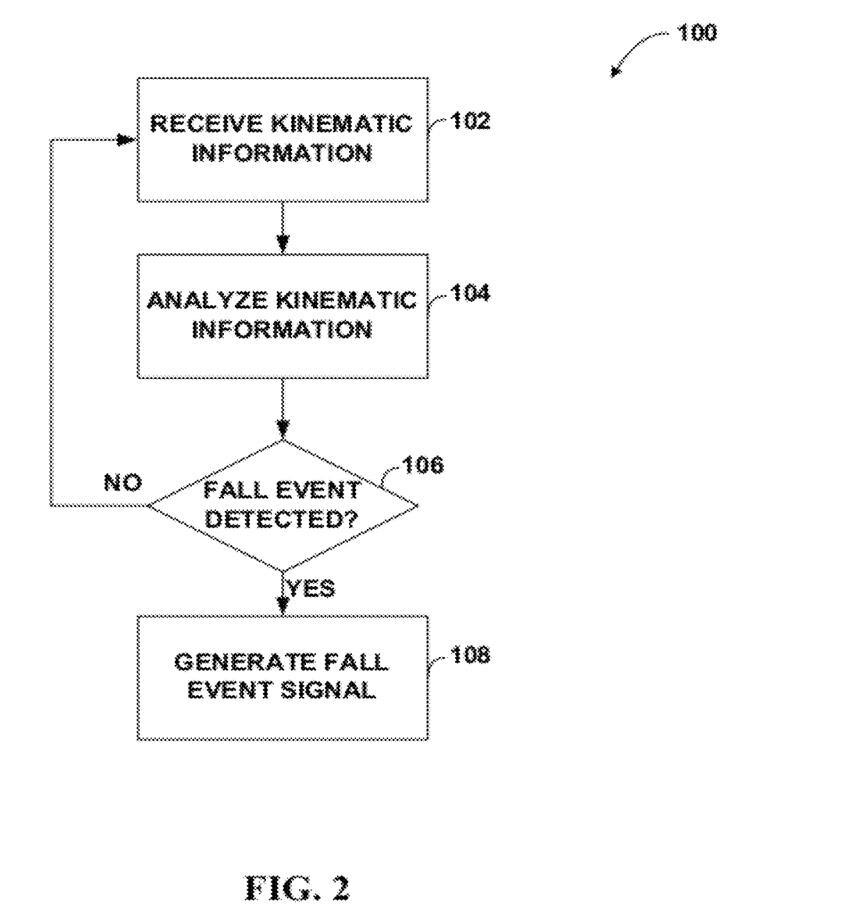
FIG. 2 is a flowchart illustrating an example process by which the fall detection device may detect a fall event.

FIG. 2 is a flowchart illustrating an example process 100 by which fall detection device 10 may detect a fall event. Process 100 is one example of a software process that may be stored in memory (such as fall detection module 30) and executed by a processor or other controller (such as controller 12) to analyze the kinematic information obtained by kinematic sensors 18 to determine whether or not a fall event has occurred. The controller receives the kinematic information from one or more kinematic sensors (such as kinematic sensors 18) (102). The controller analyzes the kinematic information to determine whether a postural disturbance will or has resulted in fall event or a recovery event (104). For example, the controller may analyze the kinematic information using an experimentally derived discriminant function, such as a linear or a quadratic discriminant function, to predict group membership (fall event versus recovery event). If a fall event is detected (106), the controller may generate a fall event signal indicating that a fall event occurred, a time/date stamp for the fall event, and/or identification of the person associated with the fall event (108).

Figure 3:
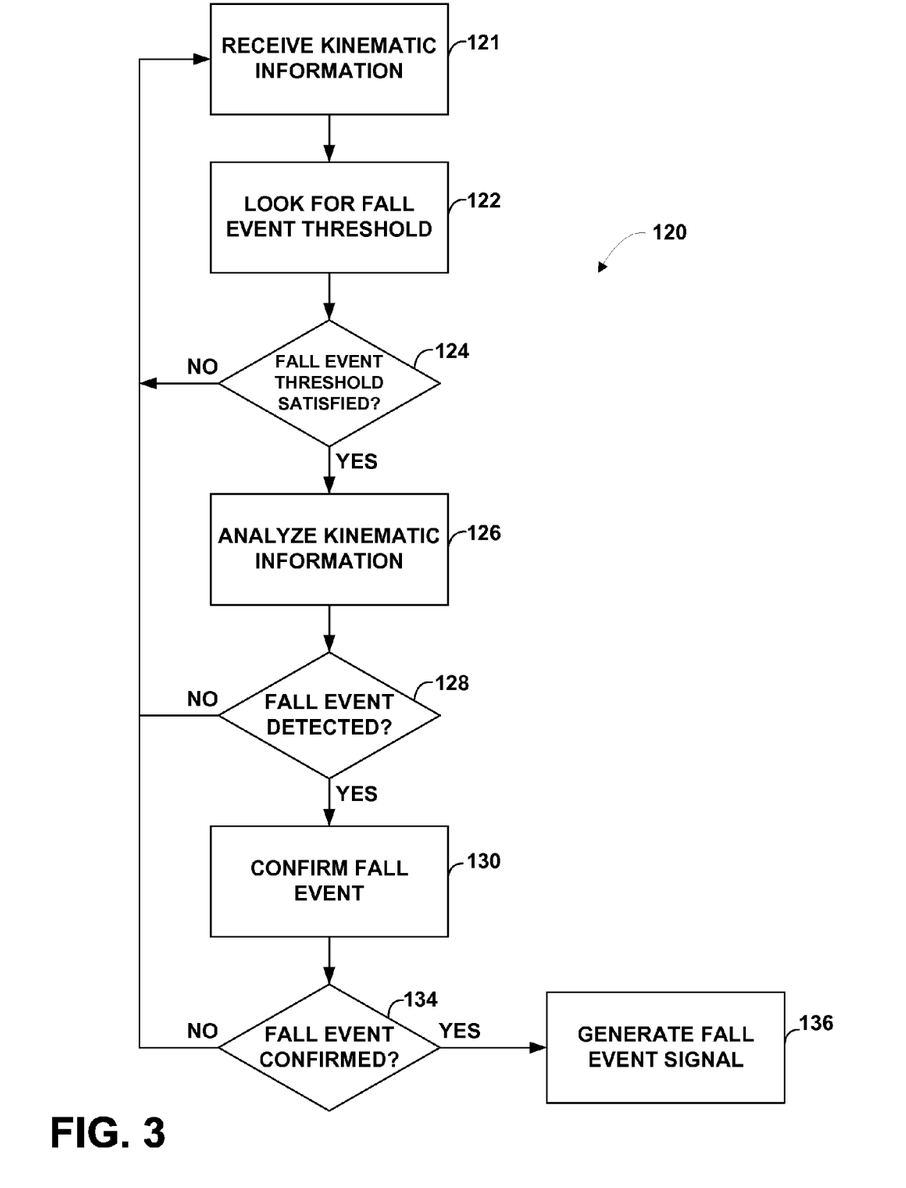
FIG. 3 is a flowchart illustrating another example process by which the fall detection device may detect a fall event.

FIG. 3 is a flowchart illustrating another example process 120 by which the fall detection device may detect a fall event. Process 120 is another example of a software process that may be stored in memory (such as fall detection module 30) and executed by a processor or other controller (such as controller 12) to analyze the kinematic information obtained by kinematic sensors 18 to determine whether or not a fall event has occurred. The controller receives the kinematic information from one or more kinematic sensors (such as kinematic sensors 18) (121). The controller may continuously sample the information received from the kinematic sensors on a periodic basis so as to continuously monitor the wearer for fall events.

The controller compares the kinematic information from at least one kinematic sensor to determine whether a fall event threshold is satisfied (122). For example, the controller may receive samples from a three-axis accelerometer capable of measuring acceleration in three orthogonal directions, the x (anteroposterior or "AP"), y (medial-lateral or "ML") and z (vertical) directions. The acceleration in any of the orthogonal directions may be compared to a fall event threshold to determine whether a postural disturbance, the magnitude of which has been experimentally determined to be sufficient to initiate a fall event, has occurred (124). If the fall event threshold is not satisfied, the controller continues to receive and monitor the kinematic information and look for postural disturbances of magnitude sufficient to satisfy the fall event threshold (121). For example, the controller may determine that the fall event threshold is satisfied when the magnitude of the postural disturbance equals and/or exceeds the fall event threshold.

The fall event threshold may be determined experimentally by exposing subjects in a sample population to a variety of postural disturbances, some of sufficient magnitude to result in a fall and others of insufficient magnitude that do not result in a fall. Whether or not the fall event threshold is satisfied (124) may be determined by comparing the measured acceleration in at least one of the AP, ML, and vertical directions with a predefined acceleration indicative of a fall in the direction at issue. For example, the fall event threshold in the forward direction (i.e., positive AP direction) may be different than the fall event threshold in the left lateral (negative ML), right lateral (positive ML), or backward (negative AP) directions. As another example, the fall event thresholds for the left lateral and right lateral directions may be of the same magnitude but have opposite signs.

If the fall event threshold is satisfied (124), the controller analyzes at least some of the kinematic information to determine whether the postural disturbance will lead to a fall event (126). In some examples, the fall detection device is able to predict whether a fall event will occur based on kinematic information identified as predictive of a fall event or a recovery event. The fall detection device may predict a fall event based on this identified kinematic information received within a few hundred milliseconds of the postural disturbance that satisfies the fall event threshold. The fall detection device analyzes the identified kinematic information and classifies the event as either a "fall event" or a "recovery event."

If the analysis classifies the postural disturbance as a recovery event (128) the process returns to receiving and monitoring the kinematic information (121). The fall detection device may, but need not necessarily, store the recovery event information, including a time/date stamp indicative of when the postural disturbance occurred.

Alternatively, if a fall event is detected (128), process 120 may instruct the controller to confirm whether an actual fall following the detection of the fall event actually occurs (130). Confirmation that a fall actually occurred may help to prevent false positives. Confirmation of an actual fall event may help to prevent fall detection device 10 from generating and transmitting a fall event signal in those situations in which the person did not actually experience a fall. To confirm the fall event, fall detection device 10 may analyze certain kinematic information received from one or more of the kinematic sensors 18 identified as being indicative of an actual fall.

If the fall event is confirmed (134), the fall detection device generates a fall event signal (136). The fall event signal may contain information indicating that a fall event occurred, a time/date stamp, identification information concerning the person associated with the fall event, and/or medical information that may be of use to assistance personnel when responding to the fall event.

Figure 4:
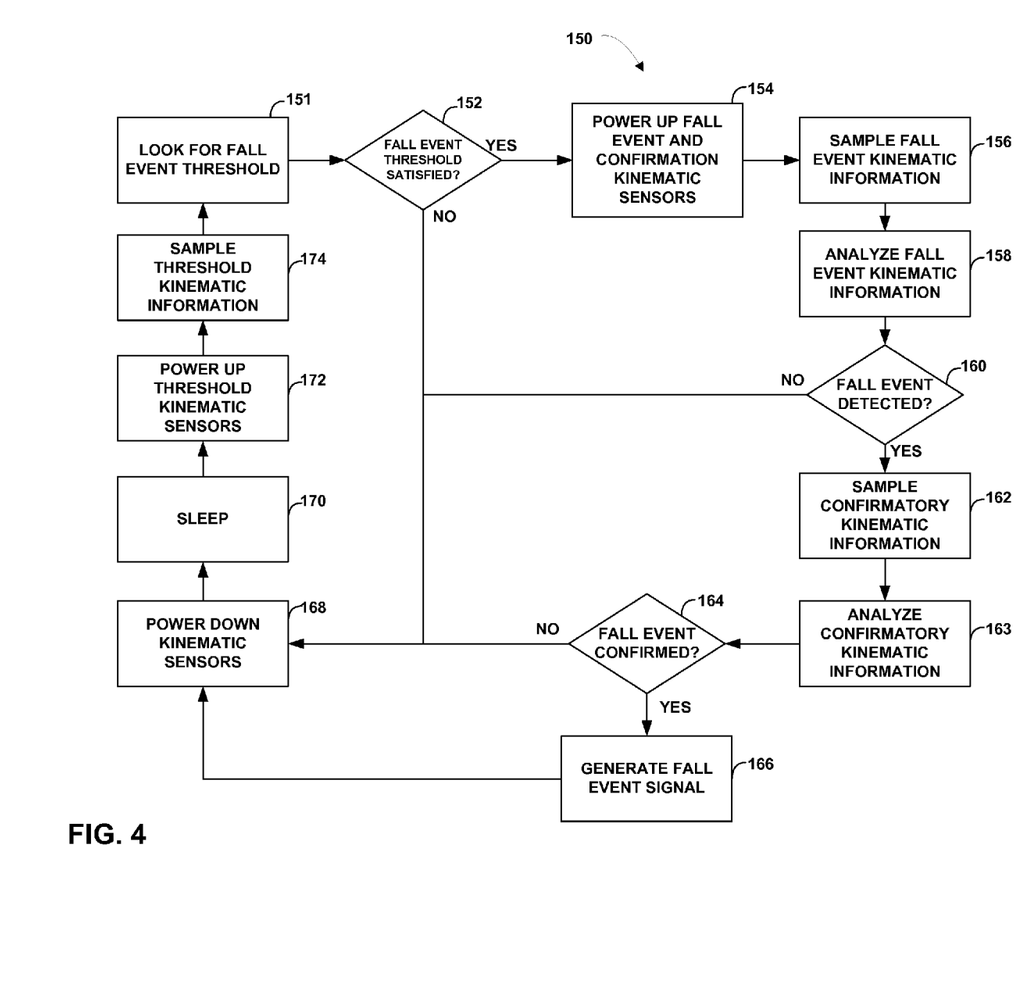
FIG. 4 is a flowchart illustrating another example process by which the fall detection device may detect a fall event.

FIG. 4 is a flowchart illustrating another example process (150) by which the fall detection device may detect a fall event. In the process of FIG. 4, more detail is shown regarding the types of kinematic information obtained. For example, the kinematic information obtained by kinematic sensors (such as sensors 18 in FIG. 1) may include one or more of threshold kinematic information, fall event kinematic information, and/or confirmatory kinematic information. The threshold kinematic information is indicative of the body's initial reaction to a postural disturbance. The threshold kinematic information (sampled at 174) may include, for example, one or more of the tri-axial accelerations of the wearer's body. The fall detection device may compare the tri-axial acceleration with a threshold in one or more of the three orthogonal directions (ML, AP, and/or vertical) to determine whether the initial threshold condition for a fall event in one or more of the three directions is satisfied.

The fall event kinematic information (sampled at 156) is analyzed to predict (within a few hundred milliseconds) whether a fall event is imminent. The fall event kinematic information may include, for example, one or more of the tri-axial acceleration, acceleration in the fall direction, vertical displacement, angular velocity, jerk (the change in acceleration per unit time), or other kinematic variables. The confirmatory kinematic information (sampled at 162) is analyzed to confirm whether the wearer actually experienced a fall event. The confirmatory kinematic information may include, for example, the absolute maximum vertical acceleration after prediction of the fall event and the vertical displacement after prediction of the fall event.

The threshold kinematic information, the fall event kinematic information and the confirmatory kinematic information may include some of the same types of kinematic information (such as acceleration in a given direction), or may include completely different types of kinematic information, or may include some of the same and some different types of kinematic information.

FIG. 4 also shows that the kinematic sensors are powered down at periodic intervals in order to preserve battery life. For example, from a sleep state (170) the kinematic sensors relevant to the fall event threshold are powered up at predetermined intervals (172). For example, the kinematic sensor(s) relevant to the fall event threshold may be a three-axis accelerometer that measures acceleration in three directions. The controller samples the kinematic information from the sensors relevant to the fall event threshold (174) and analyzes the kinematic information to determine whether the fall event threshold is satisfied (151). If the fall event threshold is not satisfied (152) the controller powers down the kinematic sensors (168) so that they are in sleep mode (170) until it is time for the next sample to be taken.

If the fall event threshold is satisfied (152), the controller powers up the kinematic sensors that measure fall event kinematic information (154). For example, in addition to the three-axis accelerometer, the controller may power up a vertical displacement sensor, one or more angular velocity sensors, or any other kinematic sensor that measures information predictive of an imminent fall event. The controller periodically samples the fall event kinematic information measured by the kinematic sensors at predetermined intervals (156). The sampling interval may be anywhere between 10-100 ms, for example. The controller then analyzes the fall event kinematic information to determine whether a fall event is imminent (158).

If a fall event is not detected (160), the controller may power down the kinematic sensors (168) and place them in sleep mode (170) until the next sampling interval. Alternatively, if a fall event is detected (160), the controller samples (162) and analyzes (163) the confirmatory kinematic information to confirm whether the wearer has actually experienced a fall event. If the fall event is not confirmed (164), the controller may power down the kinematic sensors (168) and place them in sleep mode (170).

If the fall event is confirmed (164), the controller generates a fall event signal (166). The fall event signal may contain information indicating that a fall event occurred, a time/date stamp, identification information concerning the person associated with the fall event, and/or medical information that may be of use to assistance personnel when responding to the fall event. The controller may then power down the kinematic sensors (168) and place them in sleep mode (170) until the next sampling interval.

Figure 5:
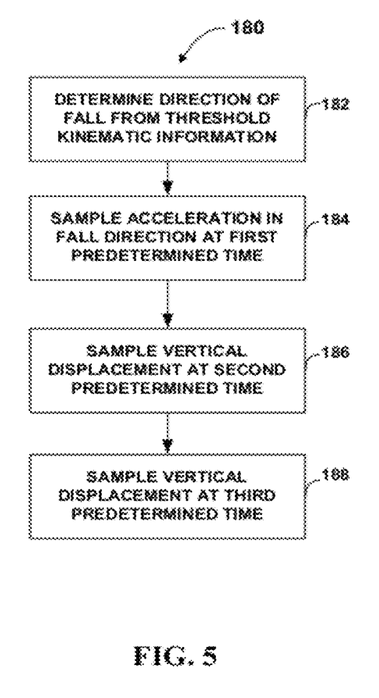
FIG. 5 is a flowchart illustrating an example process by which the controller may sample kinetic information predictive of whether a fall event is imminent.

FIG. 5 is a flowchart illustrating an example process (180) by which the controller may sample kinematic information predictive of whether a fall event is imminent. The controller may determine the direction of the fall from the threshold kinematic information (182). The direction of the fall indicated by the threshold kinematic information may be of interest because some of the fall event kinematic information predictive of a fall event (such as acceleration, velocity, and/or displacement) is also likely to be related to the fall direction. Other fall event kinematic information predictive of a fall event may not be related to the fall direction but may have a known directionality (such as vertical displacement).

For example, if the threshold kinematic information is acceleration, for example, and the kinematic threshold for acceleration in the forward direction is satisfied, the controller may determine that the fall is in the forward (positive AP) direction. Similarly, if the threshold kinematic information is acceleration, for example, and the kinematic threshold for acceleration in the left, right or backward direction is satisfied, the controller may determine that the fall is in the left, right, or backward direction, respectively. The fall direction may also be a combination of two directions, such as front/left, front/right, back/left, or back/right. Thus, when analyzing for a fall event, the controller may choose to analyze acceleration, velocity, or other kinematic variable in the fall direction to predict whether a fall event is imminent.

In addition, analysis of the experimental data may also identify the times at which certain of the fall event kinematic information is relatively more predictive of a fall event. Thus, the fall detection module may be programmed to sample one or more predetermined types of fall event kinematic information at one or more predetermined times after onset of the disturbance (that is, after the time at which the fall event threshold is satisfied). For example, based on the experimental data from a sample population, it has been found that the vertical trunk displacement at 300 ms and 350 ms after onset of the postural disturbance, e.g., fall event threshold, and the trunk acceleration in the disturbance-related direction at 300 ms after onset of the postural disturbance are kinematic variables that may be used to discriminate between a fall and a recovery in the AP direction.

In the example of FIG. 5, the controller samples the acceleration in the fall direction at a first predetermined time after onset of the postural disturbance (184). The controller may also sample the vertical displacement at a second predetermined time (186) and the vertical displacement at a third predetermined time (188). The first, second and/or third predetermined times may be equivalent or they may be different. The predetermined times may also change depending upon the fall direction (left, right, forward, backward). It shall be understood that the example shown in FIG. 5 is but one of many possible processes by which the fall detection device may gather fall detection kinematic information, and that other types of kinematic information may be gathered, and that the disclosure is not limited in this respect.

Figure 6:
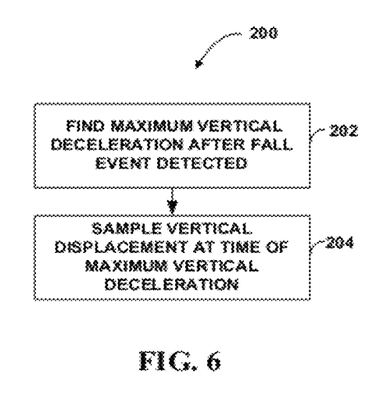
FIG. 6 is a flowchart illustrating an example process by which the controller may sample kinetic information that may confirms that the wearer actually experienced a fall event.

FIG. 6 is a flowchart illustrating an example process (200) by which the controller may sample confirmatory kinetic information that may confirm that the wearer has actually experienced a fall event. As discussed above, once the fall event threshold is satisfied (see, e.g., FIGS. 3 and 4) the kinetic sensors continue to measure the kinematic information at predetermined intervals. To confirm whether a fall event has actually occurred, the controller may analyze the confirmatory kinematic information obtained subsequent to prediction of the fall event. For example, the controller may analyze the vertical acceleration information obtained subsequent to the prediction of the fall event to identify the time at which the maximum vertical deceleration occurs (202). This corresponds to the time at which the wearer contacts the ground or the downward movement of the person is otherwise stopped. The vertical displacement of the trunk may also be sampled at the time of maximum vertical deceleration (204). This confirmatory kinematic information may then be analyzed as described above to determine whether a fall event actually occurred. As another example, instead of identifying the time at which a maximum vertical deceleration occurs, the controller may alternatively or in addition look for relatively large accelerations in any of the orthogonal directions. For example, relatively large accelerations in other than the vertical direction may be present as a person skids along the floor after landing, falls down the stairs, etc.

Referring again to FIGS. 2-4, fall detection module includes analysis of the kinematic information to determine whether a fall event will occur. As discussed above, an experimentally derived discriminant function may be used during this process. The discriminant function may be, for example, a linear discriminant function or a quadratic discriminant function. For purposes of the present description, an example using the Wald-Anderson classification statistic will be described. However, it shall be understood that other forms of discriminant analysis may also be used to predict group membership, and that the disclosure is not limited in this respect.

In some examples, if the result of the Wald-Anderson classification statistic (W) is less than zero (W<0) then a fall event is imminent. If W>0 then the algorithm determines that the subject will recover from the postural disturbance. Other variations could also be used. For example, if the signs of the coefficients were changed, a Wald-Anderson statistic where W>0 would indicate a fall event. As another example, the $\beta_0$ term could be changed so that W<100 (or W<any number) indicates a fall event.

An example Wald-Anderson classification statistic for a forward fall using acceleration data in the three orthogonal directions may given by the following equation:

$$W_{forward} = \beta_0 + \beta_1 x_1(t_0) + \beta_2 x_2(t_1 - t_0) + \beta_3 x_3(t_2 - t_0),$$

where $W_{forward}$ is the Wald-Anderson classification statistic for falls in the forward direction;

$\beta_i$ are coefficients;

$x_i$ are the tri-axial accelerations, where
  $x_1$ is the y (M/L) acceleration,
  $x_2$ is the x (AP) acceleration, and
  $x_3$ is the z (vertical) acceleration;

$t_0$ is the time at which the fall event threshold (M/L acceleration (122) in the event of a forward fall) is satisfied, and $t_1$, $t_2$, etc. are the predetermined sampling times after the threshold acceleration is satisfied.

If W<0, the algorithm determines that a fall is imminent, or If W>0, then the algorithm determines that a fall is not imminent and the subject will recover from the postural disturbance.

In this example, the Wald-Anderson classification statistic includes four terms; however, it shall be understood that the Wald-Anderson classification statistic may include more or fewer terms, and that the disclosure is not limited in this respect. In addition, although an example Wald-Anderson classification statistic for falls in the forward direction is shown above, a separate Wald-Anderson statistic may be defined for each fall direction (forward, backward, left, right). In another example, a single Wald-Anderson classification characteristic includes terms that analyzes falls in all four directions (forward, backward, left, right). As another example, the Wald-Anderson classification statistic for falls in the right and left directions may be same but with the values of certain parameters having opposite signs to account for the difference in direction. In addition, the fall event threshold for each fall direction may be different in both magnitude and direction. Also, the total number of terms, coefficients, and predetermined sampling times ($t_1$, $t_2$, ... $t_n$, etc.) may be different for each fall direction, and may be determined based on the data from the controlled laboratory tests. In this example, $x_1$ is the M/L acceleration measured at time $t_0$. The time $t_0$ is the time at which the fall event threshold is satisfied. Thus, $t_0$ defines the onset time of the postural disturbance. Although in this example the M/L acceleration is measured at the same time as the M/L threshold is determined to be satisfied (that is, at time $t_0$) this may or may not be the case for falls in the forward direction and for falls in other directions (backward, left, right). $t_0$ may be measured on the order of milliseconds. $x_2$ (AP) and $x_3$ (vertical) accelerations are measured at times $t_1$ and $t_2$, respectively, which are each defined periods of time after time $t_0$. $t_2$ and $t_3$ may also be measured on the order of milliseconds.

The times $t_0$, $t_1$ and $t_2$ at which the tri-axial accelerations are sampled may be determined based on empirical data obtained by laboratory tests conducted on a sample population in which unexpected trips are induced under controlled conditions. Tri-axial acceleration data gathered from the sample population may then be used to identify biomechanical variables causally related to the success or failure of a person in avoiding a fall after a trip. In one example, $x_1$ (M/L acceleration) may be sampled at 150 milliseconds after the onset of the disturbance and $x_2$ (AP) and $x_3$ (vertical) may be sampled at 300 milliseconds after the disturbance onset. In that example, the value assigned to each of $t_0$, $t_1$ and $t_2$ would be 150 milliseconds. However, it shall be understood that in other examples, $t_0$, $t_1$ and $t_2$ need not be equivalent, and that they may also vary depending upon the sample population. As discussed above, these predetermined times may also vary for calculations for each fall direction (forward, backward, left, right).

The $\beta_i$ coefficients of the Wald-Anderson classification statistic may be determined based on discriminant analysis of the experimental tri-axial acceleration data obtained from the sample population. More detail concerning the Wald-Anderson classification statistic is described in, for example, Morrison, D. F., *Multivariate Statistical Methods*, 2nd edition, McGraw-Hill, New York, N.Y. (1976), page 232. Although in this example the Wald-Anderson classification statistic is used to build a predictive model of group membership (fall event versus recovery event), it shall be understood that other methods for statistically distinguishing falls versus recoveries may also be used, and that other techniques be substituted for the specific technique described herein, and that the disclosure is not limited in this respect.

Another example Wald-Anderson classification statistic for a fall using acceleration data the fall direction and vertical displacement at two different times after initiation of the postural disturbance may be given by the following equation:

$$W = \beta_0 + \beta_1 x_1(t_0) + \beta_2 x_2(t_1 - t_0) + \beta_3 x_3(t_2 - t_0),$$

where
W is the Wald-Anderson classification statistic;
$\beta_i$ are coefficients;
$x_1$ is the acceleration in the fall direction,
$x_2$ and $x_3$ are vertical displacements at $t_1$ and $t_2$, respectively,
$t_0$ is the time at which the fall event threshold is satisfied, and
$t_1$, $t_2$ are the predetermined sampling times after the threshold is satisfied.

If W<0, the algorithm determines that a fall is imminent, or If W>0, then the algorithm determines that a fall is not imminent and the subject will recover from the postural disturbance.

Table 3 shows, by way of example and not by way of limitation, acceleration values (mean+/− standard deviation) that may be included in the final discriminant function for falls in the forward direction when the fall event kinematic information includes acceleration (x) at 300 ms, acceleration (y-direction) at 150 milliseconds, and acceleration (z-direction) at 300 milliseconds. Table 4 shows, by way of example and not by way of limitation, trunk COM displacement (m) and acceleration (m/s$^2$) values (mean+/− standard deviation) that may be included in the final discriminant function for forward and/or backward falls when the fall event kinematic information includes sagittal plane trunk acceleration at 300 ms, vertical trunk displacement at 300 milliseconds, and vertical trunk displacement at 350 milliseconds. It shall be understood that these values may change depending upon the sample population, on the fall direction being analyzed (forward, backward, left, right), the fall event kinematic information used, and/or other factors.

TABLE 3

| Category | $A_{x@300}$ | $A_{y@150}$ | $A_{z@300}$ |
|---|---|---|---|
| Fall | −2.4 ± 2.32 | −0.24 ± 0.71 | −5.5 ± 2.4 |
| Recovery | −0.4 ± 2.5 | 0.24 ± 1.44 | −1.7 ± 6.1 |

TABLE 4

| Variable | Fall | Recovery |
|---|---|---|
| Sagittal plane trunk acceleration at 300 ms | −1.00 ± 2.4 m/s$^2$ | −0.24 ± 0.71 m/s$^2$ |
| Vertical trunk displacement at 300 ms | 0.051 ± 0.15 m | −0.011 ± 0.042 m |
| Vertical trunk displacement at 350 ms | 0.035 ± 0.15 m | −0.015 ± 0.042 m |

Figure 7A:
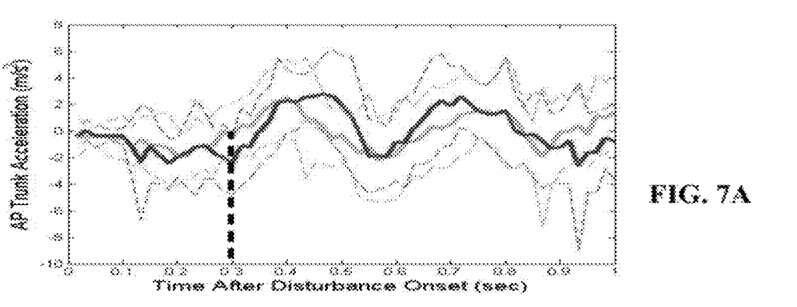
FIGS. 7A-7C are graphs illustrating example data of anteroposterior (X) (FIG. 7A), mediolateral (Y) (FIG. 7B), and vertical (Z) (FIG. 7C) accelerations of the trunk.
Figure 7B:
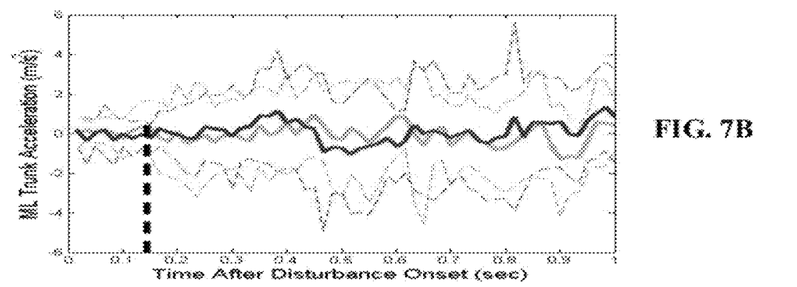
Figure 7C:
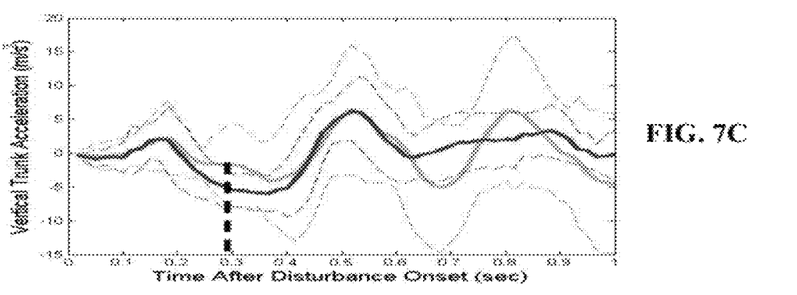

FIGS. 7A-7C are graphs illustrating example data of anteroposterior (X) (FIG. 7A), medial-lateral (Y) (FIG. 7B), and vertical (Z) (FIG. 7C) accelerations of the trunk center of mass for 1 sec after the disturbance onset. The black lines represent fall events and gray lines represent recovery events. Standard deviations are presented by the dotted lines. Vertical dashed lines represent the time points selected by the discriminant analysis in this example.

It shall be understood that, although specific values are given herein for certain of the variables involved in the fall detection algorithm, these values are given by way of example and not by way of limitation, and that the values may vary depending upon the experimental sample population. For example, the $\beta_i$ coefficients and the most relevant times $t_0$, $t_1$ and $t_2$ at which to sample the tri-axial accelerations may vary depending upon the age of the persons in the sample population, the size of the sample population, etc. The most relevant age and sample size for a particular target population to be monitored may be used to determine the most relevant fall detection algorithm for that target population. Thus, the fall detection algorithm may be adapted to be used with target populations such as the elderly, children, persons with disabilities, amputees, or any other population which would benefit from fall monitoring and detection.

One or more of the techniques described herein may be partially or wholly executed in software. For example, a computer-readable medium may store or otherwise comprise computer-readable instructions, i.e., program code that can be executed by a computer, controller or processor to carry out one of more of the techniques described herein.

For example, the systems and methods may encompass one or more computer-readable media comprising instructions that cause a processor to carry out the methods described above. A "computer-readable medium" may include but is not limited to read-only memory (ROM), random access memory (RAM), non-volatile random access memory (NVRAM), electrically erasable programmable read-only memory (EEPROM), FLASH memory, a magnetic hard drive, a magnetic disk or a magnetic tape, a optical disk or magneto-optic disk, CD, CD-ROM, DVD, a holographic medium, or the like. The instructions may be implemented as one or more software modules, which may be executed by themselves or in combination with other software, and may be executed by the controller incorporated into the body-worn unit, or by a processor not on the unit, or by some combination thereof.

The instructions and the media are not necessarily associated with any particular computer or other processing apparatus, but may be carried out by various general-purpose or specialized machines. The instructions may be distributed among two or more media and may be executed by two or more machines. The machines may be coupled to one another directly, or may be coupled through a network, such as a local access network (LAN), or a global network such as the Internet. The connections may be wired or wireless.

The techniques may also be embodied as one or more devices that include logic circuitry to carry out the functions or methods as described herein. The logic circuitry may include a processor that may be programmable for a general purpose or may be dedicated, such as microcontroller, a microprocessor, a Digital Signal Processor (DSP), an Application Specific Integrated Circuit (ASIC), a field programmable gate array (FPGA), and the like.

Various examples have been described. These and other examples are within the scope of the following claims.

The invention claimed is:

1. A device, comprising:
   at least one kinematic sensor that measures kinematic information associated with a wearer of the device, the kinematic information including threshold kinematic information and fall event kinematic information; and
   a controller that analyzes the threshold kinematic information to determine whether a threshold indicative of a postural disturbance is satisfied, and classifies the postural disturbance as a fall event or a recovery event based on the fall event kinematic information,
   wherein the controller further determines a fall direction based on the threshold kinematic information,
   wherein the fall event kinematic information includes at least one of an acceleration in the fall direction measured at a first predetermined time after onset of the postural disturbance and a vertical displacement measured at a second predetermined time after onset of the postural disturbance, and a vertical displacement measured at a third predetermined time after onset of the postural disturbance.

2. The device of claim 1 wherein the at least one kinematic sensor includes one or more of an accelerometer, a magnetometer, a pressure sensor, an altimeter, a velocity sensor, an angular velocity sensor or a gyroscope.

3. The device of claim 1 wherein the threshold kinematic information includes at least one of a displacement, a velocity, an acceleration, or a jerk.

4. The device of claim 3 wherein the threshold kinematic information includes at least one of a linear kinematic term or a rotational kinematic term.

5. The device of claim 1 wherein the fall event kinematic information includes at least one of a displacement, a velocity, an acceleration, or a jerk.

6. The device of claim 5 wherein the fall event kinematic information includes at least one of a linear kinematic term or a rotational kinematic term.

7. The device of claim 1 wherein the fall event kinematic information includes an acceleration in the fall direction.

8. The device of claim 1 wherein the kinematic information further includes confirmatory kinematic information.

9. The device of claim 8 wherein the controller further confirms whether the wearer has actually experienced a fall event based on the confirmatory kinematic information.

10. The device of claim 8 wherein the confirmatory kinematic information includes at least one of a maximum vertical deceleration and a vertical displacement measured at the time of the maximum vertical deceleration.

11. The device of claim 8 wherein the confirmatory kinematic information includes at least one of an anteroposterior (AP) acceleration, a medial-lateral (M/L) acceleration, and a vertical (z) acceleration.

12. The device of claim 8 wherein the controller further generates a fall event signal if the fall event is confirmed.

13. The device of claim 1 wherein the threshold kinematic information includes at least one of an anteroposterior (AP) acceleration, a medial-lateral (M/L) acceleration, and a vertical (z) acceleration.

14. The device of claim 1 wherein the controller detects a fall event by generating a Wald-Anderson classification statistic based on the fall event kinematic information.

15. The device of claim 14 wherein the controller detects a fall event if the Wald-Anderson classification statistic is less than 0, and determines that a fall event is not imminent if the Wald-Anderson classification statistic is greater than 0.

16. The device of claim 1 wherein the controller detects a fall event based on a discriminant function of the fall event kinematic information.

17. The device of claim 16 wherein the discriminant function is a linear discriminant function or a quadratic discriminant function.

18. The device of claim 16 wherein the discriminant function is a Wald-Anderson classification function.

19. The device of claim 1 wherein the first predetermined time comprises approximately 300 ms after onset of the postural disturbance, the second predetermined time comprises approximately 300 ms after onset of the postural disturbance, and the third predetermined time comprises 350 ms after onset of the postural disturbance.

20. A device, comprising:
    at least one kinematic sensor that measures threshold kinematic information associated with movement of a wearer of the device, the threshold kinematic information including at least one of a linear acceleration or a rotational acceleration;
    a controller that identifies a time of postural disturbance at which the threshold kinematic information satisfies a threshold indicative of a postural disturbance that may lead to the user experiencing a fall event; and
    at least one kinematic sensor that measures fall event kinematic information associated with movement of the wearer subsequent to satisfaction of the threshold, the fall event kinematic information including a linear acceleration measured at a first predetermined time after the time of postural disturbance, a vertical displacement measured at a second predetermined time after the time of postural disturbance, and a vertical displacement measured at a third predetermined time after the time of postural disturbance;
    wherein the controller further predicts whether the user will experience a fall event based on the fall event kinematic information, and determines a fall direction based on the threshold kinematic information.

21. The device of claim 20 wherein the at least one kinematic sensor that measures threshold kinematic information and the at least one kinematic sensor that measures fall event kinematic information include the same kinematic sensor.

* * * * *

UNITED STATES PATENT AND TRADEMARK OFFICE
CERTIFICATE OF CORRECTION

| | | |
|---|---|---|
| PATENT NO. | : 8,990,041 B2 | |
| APPLICATION NO. | : 13/266437 | |
| DATED | : March 24, 2015 | |
| INVENTOR(S) | : Grabiner et al. | |

It is certified that error appears in the above-identified patent and that said Letters Patent is hereby corrected as shown below:

Title Page 2, item (56), column 2, under Other Publications: "Quagliarella et al., "An Interactive Fall and Loss of Consciousness Detector System", Gait & Posture, Vol. 28, pp 603-702, 2008", should read: "Quagliarella et al., "An Interactive Fall and Loss of Consciousness Detector System", Gait & Posture, Vol. 28, pp 699-702, 2008".

Signed and Sealed this
Sixteenth Day of August, 2016

Michelle K. Lee
*Director of the United States Patent and Trademark Office*